United States Patent [19]

Paradissis et al.

[11] Patent Number: 5,133,974

[45] Date of Patent: Jul. 28, 1992

[54] EXTENDED RELEASE PHARMACEUTICAL FORMULATIONS

[75] Inventors: George N. Paradissis, St. Louis; James A. Garegnani, Ballwin; Roy S. Whaley, St. Louis, all of Mo.

[73] Assignee: KV Pharmaceutical Company, St. Louis, Mo.

[21] Appl. No.: 469,210

[22] Filed: Jan. 24, 1990

Related U.S. Application Data

[63] Continuation-in-part of Ser. No. 349,533, May 5, 1989.

[51] Int. Cl.$^5$ .............................................. A61K 09/36
[52] U.S. Cl. ...................... 424/480; 424/451; 424/456; 424/465; 424/474; 424/475; 424/494; 514/960; 514/961; 514/962; 514/963; 514/964
[58] Field of Search ............... 424/451, 456, 465, 474, 424/480, 475, 494; 514/960, 961, 962, 963, 964

[56] References Cited

U.S. PATENT DOCUMENTS

| | | | |
|---|---|---|---|
| 3,623,997 | 11/1971 | Powell | 252/306 |
| 4,000,254 | 12/1976 | Gordon et al. | 424/459 |
| 4,083,949 | 4/1978 | Benedikt | 424/459 |
| 4,173,626 | 11/1979 | Dempski et al. | 424/462 |
| 4,252,786 | 2/1981 | Weiss et al. | 424/495 |
| 4,503,031 | 3/1985 | Glassman | 424/467 |
| 4,592,753 | 6/1986 | Panoz | 424/449 |
| 4,609,542 | 9/1986 | Panoz et al. | 424/498 |
| 4,610,870 | 9/1986 | Jain et al. | 424/465 |
| 4,611,008 | 9/1986 | Heinzelmann | 514/470 |
| 4,634,587 | 1/1987 | Hsiao | 424/495 |
| 4,666,703 | 5/1987 | Kopf | 424/470 |
| 4,695,467 | 9/1987 | Uemura et al. | 424/502 |
| 4,716,040 | 12/1987 | Panoz | 424/459 |
| 4,721,619 | 1/1988 | Panoz et al. | 424/459 |
| 4,828,840 | 5/1989 | Sakamoto et al. | 424/474 |
| 4,971,805 | 11/1990 | Kitanishi et al. | 424/494 |
| 5,026,560 | 6/1991 | Makino et al. | 424/494 |

FOREIGN PATENT DOCUMENTS

| | | |
|---|---|---|
| 1183665 | 3/1985 | Canada . |
| 3048119 | 3/1984 | European Pat. Off. . |
| 0122077 | 10/1984 | European Pat. Off. . |
| 843019548 | 10/1984 | European Pat. Off. . |
| 325843 | 8/1989 | European Pat. Off. . |
| 8500481 | 3/1986 | PCT Int'l Appl. . |
| 1182124 | 2/1970 | United Kingdom . |
| 1245467 | 9/1971 | United Kingdom . |
| 2098867 | 12/1982 | United Kingdom . |
| 2141342 | 12/1984 | United Kingdom . |
| 2159715 | 12/1985 | United Kingdom . |

OTHER PUBLICATIONS

The Dow Chemical Company "Formulating for Controlled Release with METHOCEL cellulose ethers" 1987.

Copies of the PTO-1449 Forms as filed in the parent case (P6523).

Primary Examiner—Thurman K. Page
Assistant Examiner—Robert H. Harrison
Attorney, Agent, or Firm—Roper & Quigg

[57] ABSTRACT

An extended release pharmaceutical formulation adapted to approach zero order release of drug over a 12 to at least 24 hour period, comprised of a mixture of 0 to aobut 50% of an immediate release particle containing a drug, inert substrate and binder, coated with talc and up to 100% of an extended release particle comprising the immediate release particle coated with a dissolution modifying system containing plasticizers and a film forming agent.

29 Claims, No Drawings

EXTENDED RELEASE PHARMACEUTICAL FORMULATIONS

RELATED APPLICATIONS

This application is a continuation-in-part application of U.S. patent application Ser. No. 07/349,533, filed May 5, 1989, and Applicants incorporate herein by reference the entire disclosure and claims thereof.

BACKGROUND OF THE INVENTION

1 Field of the Invention

The present invention relates to extended release pharmaceutical formulations, preferably in the form of particles which are used in a tablet, capsule, or particulate form, for slowly releasing medicament over periods of time of from 12 to at least 24 hours. The extended release pharmaceutical formulations can contain both an immediate release formulation, as well as a extended release formulation, or simply the extended release formulation. The invention also relates to a method for preparing the extended release formulation and its administration to mammals.

2 Description of Related Art

It is of significant advantage to both the patient and clinician that medication be formulated so that it may be administered in a minimum number of daily doses from which the drug is uniformly released over a desired, extended period of time. Various techniques have been developed for the purpose of including a pharmaceutical preparation comprising a drug-containing particle with a coating layer and a pharmaceutical preparation comprising a continuous matrix with a drug dispersed therein, such as embedded into a rigid lattice of resinous material. In these pharmaceutical preparations, the coating layer or matrix comprises a substance insoluble, or hardly soluble, in aqueous body fluids, and the release of the drug is controlled by means of the resistance of said coating layer or matrix against the diffusion of the drug therethrough. Such pharmaceutical preparations are characterized in that the particles used in making the matrix, are made as hardly disintegratable as possible. The release of the drug from such pharmaceutical preparations is driven by the gradient of the drug concentration resulting from penetration of water by diffusion into the formulation. In this mode of release, at the latter stage of release, the rate of the release is described by Fick's law, that is, the rate of release decreases due to the decrease in the concentration gradient and the increase in the distance of the diffusion.

U.S. Pat. No. 3,458,622 to HILL discloses a controlled release tablet for the administration of medicinal agents over a prolonged period of up to about 8 hours. This patent discloses a compressed tablet for the prolonged release of a medicament containing that medicament in a core formed from a polymeric vinyl pyrrolidone, preferably polyvinyl pyrrolidone (PVP), and a carboxyvinyl hydrophilic polymer (hydrocolloid). The core material formed from the two polymeric substances provides the controlled release effect by forming a complex under the action of water or gastric fluid.

U.S. Pat. No. 4,252,786 to WEISS et al. applies a rupturable, relatively water-insoluble, water-permeable film formed of a combination of hydrophobic and hydrophilic polymers over an insoluble swelling type delayed release matrix or core containing the medicament which core includes a blend of polyvinyl pyrrolidone and a carboxyvinyl hydrophilic polymer.

U.S. Pat. No.4,140,755 to SHETH et al. discloses a sustained release formulation in the form of sustained release tablets which contain a homogeneous mixture of one or more medicaments with one or more hydrophilic hydrocolloids, such as hydroxypropylmethylcellulose having a viscosity of 4000 cps. The hydrocolloids when contacted with gastric fluid at body temperatures form a sustained gelatinous mix on the surface of the tablet causing the tablet to enlarge and acquire a bulk density of less than 1. The medicament is slowly released from the surface of the gelatinous mix which remains buoyant in the gastric fluid.

U.S. Pat. Nos. 4,309,404 and 4,248,857 to DeNEALE et al., disclose slow release formulations formed of a core material containing the active drug (31-53%), carboxypolymethylene (7-14.5%), zinc oxide (0-3%), stearic acid (4.5-10%), and mannitol (3-30%); a seal coating surrounding the core; and a sugar coating surrounding the seal coating.

U.S. Pat. No.4,309,405 to GULEY et al. discloses a sustained release tablet similar to that disclosed in DeNEALE et al. (4,304,404) except that the core contains 20 to 70% drug, 30 to 72% of a mixture of a water-soluble polymer such as hydroxypropylmethylcellulose or hydroxypropylcellulose and water-insoluble polymer (ethylcellulose alone or in admixture with carboxypolymethylene, hydroxypropylcellulose and the like).

Each of the DeNEALE et al. and GULEY et al. patents disclose that their compositions provide substantially zero order release of the core contained drug for about 12 hours following the first hour of administration. Thus, zero order release is only obtained after the initial surge of release of drug in the first hour.

U.S. Pat. No. 4,259,314 to LOWEY discloses a controlled long-acting dry pharmaceutical composition which includes a dry carrier formed from a mixture of hydroxypropylmethylcellulose (viscosity of 50 to 4000 cp in 2% aqueous solution at 20° C.) and hydroxypropylcellulose (viscosity of 4000 to 6500 cp for a 2% aqueous solution at 25° C.) which dry carrier is employed with a therapeutic agent such as aspirin, ascorbic acid and nitroglycerin.

U.S. Pat. No. 4,610,870 to JAIN et al. discloses a controlled release pharmaceutical formulation which approaches zero order release of active drug, which is provided preferably in the form of a coated tablet, containing a core portion from which medicament, such as procainamide hydrochloride, is slowly released over a controlled length of time. The core also includes one or more hydrocolloid gelling agents having a viscosity of within the range of from about 10,000 to about 200,000 centipoises in 2% solution at 20° C., such as hydroxypropylmethylcellulose and/or . methylcellulose, one or more non-swellable binders and/or wax binders (where the medicament and/or hydrocolloid gelling agents are non-compressible), one or more inert fillers or excipients, one or more lubricants, and optionally one or more antiadherents such as dioxide and water.

Enteric-coated preparations are also referred to as another type of sustained release preparation. The release of the drug from an enteric-coated preparation is delayed by providing a coating layer soluble only after arrival at the intestine, that is after the pharmaceutical preparation passes through the stomach, and the extent of this delay is determined by the rate at which the pharmaceutical preparation is generally discharged from the stomach into the intestine. By combining an enteric portion with a usable portion soluble in the stomach, the release of the drug can be rendered continuously.

U.S. Pat. No. 4,695,467 to UEMURA et al relates to a sustained release tablet which comprises easily disintegrable granules containing (a) a drug, (b) a disintegrating agent selected from the group consisting of starch derivatives, gums, cellulose derivatives and ion- exchange resins, and (c) a water-soluble polymer selected from the group consisting of cellulose derivatives, synthetic water soluble polymers and polysaccharides, the surfaces of which granules are treated with a wax selected from the group consisting of plant or animal wax, hydrogenated oils and paraffin.

SUMMARY OF THE INVENTION

In accordance with the present invention, an extended release pharmaceutical formulation is prepared which is capable of approaching zero order release of drug over a 12 to at least 24 hour period. The formulations of the present invention are composed of a mixture of 0 to 50% of an immediate release particle containing a core of drug, inert spherical substrate particles and binder, coated with talc and up to 100% of an extended release particle comprising the immediate release particle coated with a dissolution modifying system containing plasticizers and a film forming agent, wherein the particle size of the extended release formulation is $-10+60$ mesh.

The drugs used in the formulations of the invention may be selected from a wide variety of pharmaceutical formulations with particular pharmaceutical compounds being analgesics, anti-inflammatories, antihistamines, antitussives, expectorants, decongestants, narcotics, antibiotics, bronchodilators, cardiovasculars, central nervous system (CNS) drugs, metal salts, minerals, vitamins and mixtures thereof.

Another embodiment of the invention involves a process for preparing an extended release pharmaceutical formulation for oral administration which comprises:

a) forming a core material by spraying a solvent containing a dissolved binder onto a mixture of at least one drug and inert spherical substrate particles;

b) drying the resulting mixture to form a core material and coating the core material with talc;

c) coating the immediate release particles by spraying the particles with a dissolution modifying system containing plasticizer and film forming agent to form an extended release pharmaceutical formulation; and d) recovering the formed extended release pharmaceutical formulation having sizes from $-10+60$ mesh, U.S. Standard sieve size.

In an alternate embodiment, the invention involves orally administering to a mammal the extended pharmaceutical formulation to enable a 12 to at least 24 hour drug release therapy to be achieved.

DESCRIPTION OF THE PREFERRED EMBODIMENTS

The extended release pharmaceutical formulations of the present invention comprise from 0 to 50% of an immediate release particle containing a core of at least one drug; and up to 100% of an extended release particle which comprises the immediate release particle additionally coated with a dissolution modifying system and optionally additional drug.

The immediate release particles contain a core of at least one drug, inert spherical substrate particle and binder which is coated with talc. The immediate release particles have a preferred size of $-10+60$ U.S. Standard mesh size. With regard to the extended release particles, such particles comprises the aforementioned immediate release particles with an additional coating of a dissolution modifying system containing plasticizers and a film forming agent, which particles likewise have a preferred particle size of $-10+60$ U.S. Standard mesh sieve size.

The immediate release particle containing drug, inert spherical substrate and binder can be prepared in any conventional manner known for producing particles. For example, they may be produced in a conventional coating pan or other equipment, such as a rotor-granulator, merumerizer or fluidized bed spray coater.

In a preferred procedure, the inert spherical substrate is placed in a coating apparatus and the solid particles of pharmaceutical (drug) product are fed into the apparatus while being sprayed with a solution containing the binder. The binder, when applied, results in the formation of particles which may then be easily coated with a talc coating which is likewise mixed with the same solution used above.

A wide variety of medicaments which are orally administered both in tablet, capsule and particulate form may be used to prepare the particles according to this invention. These include drugs from all major categories, and without limitation, for example, analgesics, such as acetaminophen, ibuprofen, flurbiprofen, ketoprofen, voltaren (U.S. Pat. No. 3,652,762), phenacetin and salicylamide; anti- inflammatories selected from the group consisting of naproxen and indomethacin; antihistamines, such as chlorpheniramine maleate, phenindamine tartrate, pyrilamine maleate, doxylamine succinate, phenyltoloxamine citrate, diphenhydramine hydrochloride, promethazine, brompheniramine maleate, dexbrompheniramine maleate, clemastine fumerate and triprolidine; antitussive selected from the group consisting of dextromethorphan hydrobromide and guaifenesin; expectorants such as guaifenesin; decongestants, such as phenylephrine hydrochloride, phenylpropanolamine hydrochloride, pseudoephedrine hydrochloride, ephedrine; narcotics, such as morphine, and codeine and their derivatives, such as oxycodone and hydromorphone; antibiotics such as erythromycin, penicillins and cephalosporins and their derivatives; bronchodilators such as theophylline, albuterol and terbutaline; cardiovascular preparations such as diltiazem, propranolol, nifedepine and clonidine; central nervous system drugs such as such as thioridazine, diazepam, meclizine, ergoloid mesylates, chlorpromazine, carbidopa and levodopa; metal salts such as potassium chloride, and lithium carbonate; minerals selected from the group consisting of iron, chromium, molybdenum and potassium; and vitamins selected from water-soluble vitamins such as B complex, vitamin C, vitamin B12 and folic acid.

Particularly preferred dosage forms involve use of pseudoephedrine hydrochloride; pseudoephedrine hydrochloride and chlorpheniramine maleate; and phenylpropanolamine hydrochloride and chlorpheniramine maleate, all of which have been found to exhibit the following dissolution ranges:

| | |
|---|---|
| Hour 1 | 0-50% |

| -continued | |
|---|---|
| Hour 8 | 50-80% |
| Hour 12 | NLT 65% |

It should be recognized that these drugs are representative and are not intended to limit the scope of the invention. The drugs are employed in amounts to provide a therapeutically effective dose and are preferably present in amounts of about 4 to about 85% by weight of the final formulation, and most preferably from about 40 to about 55% by weight.

When small amounts of a particular drug are used, that is amounts below about 50 mg per dosage form, (either alone or in combination with other drugs) it is advantageous to employ an optional carrier to aid in uniformly distributing the drug throughout the dosage form. Such carriers assist in bulking the drug to make it easier to be applied to the inert substrate. Exemplary carriers include sugar, lactose, gelatin, starch, and silicon dioxide. When employed, they are present in amounts of about 0.01 to about 15% by weight of the final product.

The immediate release particle core additionally contains an inert spherical substrate particle which aids in the diffusion/release of the drug from the formulation. The inert so that the rate of drug release is not variable. In general, smaller particles result in rapid diffusion of drug, whereas larger particles result in a delay of drug diffusion. Suitable materials may be selected from sugar spheres and other substances which would not modify the drug release pattern or be reactive with the active component, such as non-toxic plastic resin beads. The inert spherical substrate particles are employed in the core of the immediate release particles in amounts of about 15 to about 40% by weight, and preferably in amounts of about 20 to about 35% by weight of the total formulation.

The drug adheres to the inert spherical substrate particle through a binding agent which is preferably applied by a suitable solvent. Water is the preferred solvent for water-soluble binders, whereas organic solvents are used with organic soluble binders. Binders may be selected from a wide range of materials such as hydroxy- propylmethylcellulose, ethylcellulose, or other suitable cellulose derivatives, povidone, acrylic and methacrylic acid co-polymers, or pharmaceutical glaze. Exemplary solvents are water, ethanol, isopropyl alcohol, methylene chloride or mixtures and combinations thereof.

The binders are generally employed in small amounts which are just suitable to retain the drug on the inert spheres. Useful amounts may vary from about 0.5 to about 4% by weight, and preferably from about 1 to about 2% by weight of the total formulation.

The binder is preferably applied to the drug and inert spherical substrate in solution form. This may be achieved by dissolving the binder in either water or a suitable organic solvent such as isopropyl alcohol. When used as a solution, the solution generally contains from about 2 to about 25% binder and remainder solvent.

Once the initial core material has been prepared, it is important to dry the material prior to it being coated with a coating layer of talc. This may be conveniently done by passing air over the particles, or by simply pan drying overnight. After the core has been dried, it is mixed with powdered talc and again sprayed with the binder solution, as described above to coat the core with the talc. The talc is generally employed in amounts suitable to prepare the surface of the particles to receive the dissolution modifying system coat, to prevent the drug layer from interfering with film formation on the particles and to prevent drug migration during storage. This is achieved by using amounts of talc of about 4 to about 20% and preferably of about 5 to about 18% by weight of the final product.

After the talc is applied, the resulting product is dried and classified by size to recover particles having sizes from −10+60 mesh, U.S. Standard mesh size. This particle size is essential to prepare an extended release particle that functions properly in the inventive formulations.

The resulting product comprises a talc coating adhered to a core particle comprising the inert spherical substrate layered with the active pharmaceutical compound.

The extended release particles of the invention are then prepared by taking the immediate release particles and coating them with a dissolution modifying system which functions as a diffusion membrane around the coated core. The dissolution modifying system by spraying the immediate release particles with about 2 to about 35% by weight of the dissolution modifying system coating.

The dissolution modifying system is designed to encapsulate the particles and modify the drugs dissolution profile so that a sustained/extended drug release rate is obtained. In other words, the system is formulated to each drug profile to permit a release of the drug from the particles over a 12 to at least 24 hour period.

The rate of release of the pharmaceutical formulation may be described according to standardized dissolution testing procedures as found in the U.S. Pharmacopoeia XXII, where less than 50% of the drug is released within 1 hour of measurement and not less than 70% of the drug is released at the targeted dosing period, such as a 12 to at least 24 hour period.

The plasticizers used in the dissolution modifying system are preferably previously dissolved in an organic solvent and applied in solution form. Preferred plasticizers may be selected from the group consisting of diethyl phthalate, diethyl sebacate, triethyl citrate, crotonic acid, propylene glycol, butyl phthalate, dibutyl sebacate, castor oil and mixtures thereof. As is evident, the plasticizers may be hydrophobic as well as hydrophilic in nature. Water-insoluble hydrophobic agents, such as diethyl phthalate, diethyl sebacate and castor oil are used to delay the release of water-soluble drugs, such as potassium chloride. In contrast, hydrophilic plasticizers are used when water-insoluble drugs are employed which aid in dissolving the encapsulating film, making channels in the surface, which aid in drug release. In this regard, a system can be tailored to a particular drug which will be able to form or not form pores to permit the proper drug release profile to be achieved.

The plasticizers are generally employed in amounts of about 0.01% to about 5% by weight of the total formulation. If too much is employed in a particular modifying system the drug will release too quickly from the structure. In contrast, if not enough is employed, the coating may not be strong enough and it becomes brittle.

The film forming agents, which are also preferably employed in a spraying solution along with the plasticizer, may be selected from a wide variety of film forming materials. Preferable materials, however, may be selected from the group consisting of acrylic and methacrylic acid copolymers and cellulose derivatives. Exemplary cellulose derivatives include ethylcellulose, methylcellulose, cellulose acetate, hydroxypropylcellulose, hydroxypropylmethylcellulose, hydroxyethylcellulose and mixtures thereof. The film forming agents are employed in amounts of about 0.5 to about 25% by weight of the total formulation.

Furthermore, the dissolution membrane system may include porosity modifying agents, such as talc and salts of fatty acids, such as calcium stearate. Useful amounts of up to about 25% by weight of the final product have been found effective when used. Once the extended release particles are formed, they are dried by removing the solvents by conventional drying means, such as pan drying or air drying. Once the particles are prepared and dried, they are removed from the coating pan or fluidized bed spraying apparatus, and passed through an appropriate screen in order to recover the material that is sized between −10+60 mesh, U.S. Standard sieve. The coating membrane may also include additional amounts of drug beyond that present in the core or different drug which may be incompatible with the core drug.

It should be noted that the particle size of the particles which are used in finally preparing the invention particles can have a significant impact on the release rate of the drug. In particular it is essential to use starting components of drug and inert carriers which have mesh sizes greater than 200 mesh. Such sizes aid in offering various advantages. First, they assist in making hard granules which improves the binding characteristics of the matrix. Secondly, the particle size affects the final product particle size which can greatly influence the rate at which the polymer hydration or gel formation occurs in the capsule, tablet or particle surface. In general, particle sizes outside the ranges disclosed herein are unsuitable for preparing an extended release pharmaceutical formulation.

By employing the formulations of the invention, one is able to achieve an extended release system which is a dynamic system composed of wetting, hydrating and dissolution components. At the same time, other soluble materials or drugs will also wet, dissolve and diffuse out of the matrix while insoluble materials will be held in place until the surrounding encapsulation layer erodes or dissolves away.

The extended release pharmaceutical formulations of this invention exhibit dissolution patterns which result in the reduction of various side effects associated with the normal use of such drugs. For example, cough/cold formulations containing pseudoephedrine hydrochloride are known to cause central nervous system disorders, such as enhanced agitation and insomnia. Such formulations when used according to the invention show significantly reduced side effects. In the case of potassium chloride which is a known gastrointestinal irritant, such irritation is significantly reduced when the metal salt is administered using the system of this invention. These same unexpected advantages would be expected to occur with the other pharmaceutical drugs and materials that are useful herein.

The extended release pharmaceutical formulation of the present invention may be comprised of two main components: the immediate release particles and extended release particles. The immediate release particles and extended release particles may be blended together and filled into hard gelatin capsules or formed into tablets with standard equipment.

A particularly preferred extended release pharmaceutical formulation according to the invention is comprised of a mixture of:

a) 0 to about 50% of an immediate release particle containing about 15 to about 40% by weight inert spherical substrate particle, about 0.5 to about 4% binder and about 4 to about 75% of at least one drug and a coating comprising about 4 to about 20% talc; and b) up to 100% of an extended a controlled release particle comprising an immediate release granule of a) coated with a dissolution modifying system comprising about 0.5 to about 25% film forming agent, about 0.01 to about 5% plasticizer and up to 25% modifying agent; all percents herein are by weight of the final product.

Batch sizes may vary depending on the capacity and type of equipment used. Quantities of ingredients likewise can be varied with specified ranges to assure that the product meets the desired dissolution and potency characteristics. The following procedure describes one set of conditions and is not intended to be limiting thereto.

A preferred process for preparing the formulations of this invention may be described as follows:

1. Preparation of Core Material

Suitable amounts of drug are weighed and pulverized so that the mesh size is greater than 200 mesh. The solution of binder is prepared by mixing a suitable binder into a suitable solvent. The inert spherical substrate particles (such as sugar spheres) are placed in a suitable coating pan. The pharmaceutical drug is added to the pan and the binder solution is sprayed onto the mixture. The spray system should be designed such that the solution is sprayed at a controlled rate over a designated period of time. This process is controlled until all of the active powder has been applied in each pan. The core particle is then dried.

2. Application of Talc Coat

After the core has been dried, powdered talc is added to the core and mixed, whereupon a second spray solution is applied to result in the coating of the core with the talc. Once the talc has been applied, the particles are removed and dried in a suitable dryer, such as an air dryer, at ambient to 80° C. for a minimum of 6 hours. The granules are then passed through a suitable sizing sieve in order to isolate those particles having mesh sizes of −10+60 mesh.

3. Application of Dissolution Modifying Coating

A portion of the immediate release granules obtained from the prior procedure are placed in a suitable coating pan. They are then optionally dry mixed with powdered talc and an optional lubricant, such as calcium stearate. Once blended, the admixture is sprayed with the encapsulation solution containing the plasticizer and film forming agent. An exemplary system would include ethylcellulose as the film forming agent, isopropyl alcohol, and methylene chloride as solvents, and diethyl phthalate as the plasticizer, for water-soluble drugs such as pseudoephedrine hydrochloride. The amount of powdered talc and calcium stearate applied to the immediate release particles will vary depending on the drug release profile desired. After coating and drying of the extended release particles, the particles are again sized and those particles falling between −10 and +60 mesh are recovered. The samples recovered are submitted to analytical assay for potency, extended release pattern and residual solvent testing. Based upon the assay report and sustained release pattern, additional extended release coatings may be applied.

4. Product Formulation

Based upon the assay results and total drug activity and controlled release pattern, the appropriate amounts of immediate and extended release particles are mixed to achieve the desired activity and release pattern. The formulation may be then tableted with well known and suitable excipients and filler materials, or filled in capsules such as hard gelatin capsules by well-known means. Clearly, if based on activity and release pattern, a greater release is required during the early hours, additional immediate release particles of from 0 to 50% by weight may be blended with the extended release particles which are present in amounts up to 100% by weight; or if less release is required, the immediate release particles can be blended with additional extended release particles to reduce the proportion of immediate release particles that are present.

The formulations of the invention are administered orally to mammals in suitable amounts to achieve the drug efficacy sought. When administered in proper dosage forms, the formulations are able to deliver the drugs in zero order release rates to achieve from about 12 to 24 hours drug delivery.

The present invention is further illustrated by the following examples. All percentages used throughout the specification and claims are based on the weight of the final product, unless otherwise indicated, and all formulations total 100% by weight.

| EXAMPLE 1 PSEUDOEPHEDRINE HYDROCHLORIDE 240 mg EXTENDED-RELEASE CAPSULE ||
| --- | --- |
| Composition | % |
| Pseudoephedrine Hydrochloride, USP | 45.28 |
| Sugar Spheres, NF | 15.12 |
| Talc, USP | 15.32 |
| Povidone, USP | 0.35 |
| Pharmaceutical Glaze, NF | 1.80 |
| Calcium Stearate, NF | 3.08 |
| Ethylcellulose, NF | 1.55 |
| Diethyl Phthalate, NF | 0.02 |
| Sugar Spheres, NF-QS | 17.48 |
|  | 100.00 |

The pseudoephedrine hydrochloride is pulverized and applied on the sugar spheres using 0.178 cc/capsule of a solution comprised of 31.8% v/v 2 lb. cut pharmaceutical glaze (prepared by diluting 4 lb. cut pharmaceutical glaze with an equal volume of isopropyl alcohol), 13.6% v/v 10% povidone solution in isopropyl alcohol, 9.1% v/v water, 45.5% v/v isopropyl alcohol.

The so prepared particles are dried to remove the residual solvents at temperatures up to 80° C.

To these dried particles, an inert seal coat of 32.18 mg of talc with 0.025 cc/capsule of the same solution as used for the application of the pseudoephedrine hydrochloride is applied. After the inert seal is applied, the particles are dried again to remove any residual solvents at varying temperatures up to 80° C.

To the above particles the diffusion control membrane is applied. The solution of this membrane is composed of 5% w/w ethylcellulose with 0.1% w/w diethyl phthalate in a co-solvent system composed of 2 parts of isopropyl alcohol and 1 part methylene chloride, applied with 49 mg of talc and the calcium stearate. The so prepared particles are dried to remove any residual solvents at temperatures up to 80° C.

These extended release particles are blended with the immediate release particles and tested by a USP XXII method with the following results:

| DISSOLUTION RESULTS OF EXAMPLE 1 ||
| --- | --- |
| Time (h) | % of release |
| 1 | 25 |
| 4 | 40 |
| 8 | 65 |
| 12 | 81 |
| 24 | 97 |

The pseudoephedrine capsules produced were tested for central nervous system (CNS) side effect reduction in a double blind clinical study in humans against a commercially available pseudoephedrine 120 mg capsule dosed twice a day. The study indicated that the capsules produced by this invention had reduced CNS related side effects. More specifically, the pseudoephedrine capsules, produced in accordance with Example I, were reported to have incidents of agitation and insomnia of 81% and 71% less, respectively as compared to the 120 mg capsule while the efficacy was maintained.

SUMMARY OF CLINICAL STUDY

Pseudoephedrine 240 mg. Once-A-Day vs. Placebo

4 Multi-Center Studies

Double-Blind conditions: Identically appearing capsules

Duration: 3 weeks

Patients: (moderate to severe nasal congestion)

|  | Pseudoephedrine | Placebo | Total |
| --- | --- | --- | --- |
| Males/Females | 226 (109/117) | 217 (115/102) | 443 (224/219) |

Efficacy Parameters & Results

Patient Diary Data: Symptoms assessed daily. Patients in the Pseudoephedrine group had significantly less severe nasal congestion ($p < 0.05$).

Global Assessments: Patient and investigator assessments of nasal congestion were better for Pseudoephedrine group; the difference was statistically significant ($p < 0.05$).

| EXAMPLE 2 PSEUDOEPHEDRINE HYDROCHLORIDE 240 mg/ CHLORPHENIRAMINE MALEATE 24 mg EXTENDED-RELEASE CAPSULE ||
| --- | --- |
| Composition | % |
| Pseudoephedrine Hydrochloride, USP | 44.04 |
| Chlorpheniramine maleate, USP | 4.40 |
| Sugar Spheres, NF | 22.01 |
| Talc, USP | 9.86 |
| Calcium Stearate, NF | 8.61 |
| Povidone, USP | 1.57 |
| Ethylcellulose, NF | 2.84 |
| Diethyl Phthalate, NF | 0.06 |
| Sugar Spheres, NF-QS | 6.61 |
|  | 100.00 |

The pseudoephedrine hydrochloride and chlorpheniramine maleate are pulverized and then blended together and applied to the sugar spheres using 0.178 cc/capsule of a 10% povidone solution in isopropyl alcohol.

The so prepared particles are dried to remove the solvents at temperatures up to 80° C.

To these dried particles, an inert seal coat of 38.1 mg of talc with 0.021 cc/capsule of a 10% povidone solution in isopropyl alcohol is applied. After the inert seal is applied, the particles are dried again to remove any residual solvents at varying temperatures up to 80° C.

To the above particles the diffusion control membrane is applied. The solution of this membrane is composed of 5% ethylcellulose with 0.1% diethyl phthalate in a co-solvent system composed of 2 parts of isopropyl alcohol and 1 part methylene chloride, applied with 15.65 mg of talc and the calcium stearate. The so prepared particles are dried to remove any residual solvents at temperatures up to 80° C.

These extended release particles are blended with the immediate release particles and tested as previously described.

| Time (h) | DISSOLUTION RESULTS OF EXAMPLE 2 | |
|---|---|---|
| | Pseudoephedrine Hydrochloride % Released | Chlorpheniramine Maleate % of release |
| 1 | 25 | 24 |
| 4 | 39 | 42 |
| 8 | 69 | 68 |
| 12 | 84 | 80 |
| 24 | 96 | 90 |

| EXAMPLE 3 | |
|---|---|
| Composition | % |
| Phenylpropanolamine Hydrochloride, USP | 42.25 |
| Chlorpheniramine Maleate, USP | 6.76 |
| Sugar Spheres, NF | 22.54 |
| Talc, USP | 7.15 |
| Ethylcellulose, NF | 10.87 |
| Stearic Acid, NF | 4.35 |
| Polyethylene Glycol, NF | 2.17 |
| Povidone, USP | 1.43 |
| Mineral Oil, USP | 1.09 |
| Triethyl Citrate, NF | 1.39 |
| | 100.00 |

The phenylpropanolamine hydrochloride and chlorphenir- amine maleate are pulverized and then blended together and applied to the sugar spheres using 0.128 cc/capsule of a 47.5% w/w isopropyl alcohol, and 5.0% w/w water.

The so prepared particles are dried to remove the solvents at temperatures up to 80° C.

To these dried particles, an inert seal of talc with 0.010 cc/capsule of the same solution as described above is applied. After the inert seal is applied, the particles are dried again to remove any residual solvents at varying temperatures up to 80° C.

To the above particles the diffusion control membrane is applied. The solution of this membrane is composed of 5% w/w ethylcellulose, 2% w/w stearic acid, 1% w/w polyethylene glycol, 0.5% w/w mineral oil, 0.64% w/w triethyl citrate, 39.16% w/w methylene chloride, 51.7% w/w isopropyl alcohol. The so prepared particles are dried to remove any residual solvents at temperatures up to 80° C.

These extended release particles are blended immediate release particles and tested for dissolution and tested by the revolving bottle method with the following results:

| DISSOLUTION RESULTS OF EXAMPLE 3 | | |
|---|---|---|
| Time (h) | Phenylpropanolamine Hydrochloride % Released | Chlorpheniramine Maleate % of release |
| 1 | 21 | 21 |
| 8 | 67 | 66 |
| 12 | 81 | 77 |
| 24 | 94 | 89 |

| EXAMPLE 4 | |
|---|---|
| Potassium Chloride 10 mEq Extended-Release Capsule | |
| Composition | % |
| Potassium Chloride, USP | 77.72 |
| Talc, USP | 7.77 |
| Ethylcellulose, NF | 2.81 |
| Dibutyl Sebacate | 0.02 |
| Diethyl Phthalate, NF | 0.04 |
| Calcium Stearate, NF | 6.27 |
| Sugar Spheres, NF | 5.37 |
| | 100.00 |

Talc is applied onto the potassium chloride crystals using 0.213 cc/capsule of a solution composed of 5% w/w ethylcellulose with 0.1% w/w dibutyl sebacate dissolved in 34.9% w/w methylene chloride, and 60.0% w/w isopropyl alcohol.

The so-prepared particles are dried to remove the residual solvents at temperatures up to 80° C.

To these dried particles, the diffusion control membrane is applied. The solution of this membrane is composed of 5% w/w ethylcellulose with 0.1% w/w diethyl phthalate, in a co-solvent system composed of 2 parts isopropyl alcohol and 1 part methylene chloride, applied with 61 mg. of calcium stearate. The so-prepared particles are dried to remove any residual solvents at temperatures up to 80° C.

These extended-release particles may be blended with the immediate release particles and tested for dissolution with the following results:

| Dissolution Results Example | |
|---|---|
| Time (h) | % of Release |
| 1 | 5 |
| 8 | 34 |
| 16 | 58 |
| 24 | 75 |
| Hour | Range of Dissolution |
| 1 | 0–50% |
| 8 | 20–70% |
| 24 | NLT 60% |

Gastrointestinal Blood Loss

In one investigation for gastrointestinal irritation, 32 swine were used. In this study, the swine were sacrificed and the gastrointestinal track was examined. In the placebo and the potassium chloride capsules of this invention, no significant lesions were observed in the swine. Microscopic lesions were apparent in the animals treated with Slow-K ® tablets and Micro-K ® capsules.

Capsules produced by this invention were less irritating than these other commercially available potassium chloride controlled release preparations at comparable dose levels. See Example 6.

EXAMPLE 5
Potassium Chloride 10 mEq Extended-Release Capsules

| Composition | % |
| --- | --- |
| Potassium Chloride, USP | 77.72 |
| Povidone, USP | 0.25 |
| Talc, USP | 3.9 |
| Hydroxypropyl Methyl Cellulose, USP | 0.14 |
| Methacrylic Acid Co-polymer, NF | 0.74 |
| Polyethylene Glycol, NF | 0.07 |
| Calcium Stearate, NF | 3.70 |
| Sugar Spheres, NF | 13.43 |
| | 100.00 |

A portion of the potassium chloride is pulverized and applied on the remaining potassium chloride crystals using 0.178 cc/capsule of a 10% povidone solution in isopropyl alcohol.

The so-prepared particles are dried to remove the solvents at temperatures up to 80° C.

To these dried particles, an inert seal coat of 37.6 mg of talc with 0.055 cc/capsule of a solution composed of 2.5% w/w hydroxypropyl methylcellulose dissolved in 40% w/w methylene chloride and 57.5% w/w isopropyl alcohol.

The so-prepared particles are dried to remove the solvents at temperatures of up to 80° C.

To these dried particles, the diffusion control membrane is applied. The solution of this membrane is composed of 1% w/w methacrylic acid co-polymer with 0.1% w/w polyethylene glycol and w/w calcium stearate in a co-solvent system composed of 53.9% w/w isopropyl alcohol and 40.0% w/w methylene chloride. The so-prepared particles are dried to remove any residual solvents at temperatures up to 80° C.

These extended-release particles may be blended with the immediate release particles and tested for dissolution by a USP XXII method with the following results:

| Dissolution Results Example | |
| --- | --- |
| Time (h) | % of Release |
| 1 | 25 |
| 4 | 70 |
| 12 | 100 |
| Hour | Range of Dissolution |
| 1 | 0-50% |
| 4 | 40-90% |
| 12 | NLT 65% |

EXAMPLE 6

Controlled release potassium chloride by this invention as hereinafter described was tested in 38 humans in a four-way parallel study to determine the average fecal blood loss from each product. In order to demonstrate maximum safety, the product of this invention was dosed at four times the level of potassium chloride as the commercial products tested per dosing interval, yet indicating significant reduction in gastrointestinal irritation.

Human Studies
A. EXPERIMENTAL DESIGN/METHODS

The effect on gastrointestinal blood loss of orally administered inventive potassium chloride capsules, Micro-K ® capsules, Slow-K ® tablets, aspirin and placebo was investigated in a study on humans.

The subjects were 40 healthy caucasian males; they ranged in age from 18-55 years. On the basis of a history and laboratory and physical examinations performed within two weeks of study initiation, it was concluded that all subjects met all study admission criteria.

The subjects were sequestered for the duration of the study, and a parallel design was employed. During two treatment periods (each seven days long, the first of which was preceded by a three-day period during which treatment was withheld), the subjects received appropriate daily oral doses of placebo and then one of the test drugs. Each subject collected his 24-hour stool sample and delivered the samples to laboratory personnel each day. Blood samples were obtained from each subject at weekly intervals. The subjects were provided with a standardized diet, were told not to use drugs other than those dispensed to them by laboratory personnel, and were given a soft toothbrush.

B. RESULTS AND CONCLUSIONS

Thirty-eight of the 40 subjects completed the study as scheduled; two of the subjects left the study site early, on study day 18 (after providing the scheduled blood sample). Daily fecal blood volumes averaged 0.28 and 0.52, 0.28 and 0.50, 0.36 and 0.54, and 0.40 and 6.63 ml during periods of treatment with placebo and inventive potassium chloride capsules, placebo and Slow-K ® tablets, placebo and Micro-K ® capsules, and placebo and aspirin, respectively. The results observed during periods of treatment with aspirin validate the methodology.

Statistical analysis revealed that the average daily fecal blood volumes observed during periods of treatment with placebo did not differ from each other, that the average daily fecal blood volumes observed during periods of treatment with the three potassium chloride formulations did not differ from each other (despite the fact that the fractional doses of Micro-K ® capsules and Slow-K ® tablets were less than one-fourth the once daily dose of inventive potassium chloride capsules), and that the differences between the average daily fecal blood volumes observed during periods of treatment with placebo and the three potassium chloride formulations did not differ from each other. These results indicate that the greater patient compliance, which can be expected to result from the once daily dosing with inventive potassium chloride capsules, will not come at the cost of increased gastrointestinal toxicity.

We claim:

1. An extended release pharmaceutical formulation for oral administration, which comprises: a pharmaceutical formulation which is adapted to approach zero order release of drug over a 12 to at least a 24 hour period, which formulation is comprised of a mixture of a) about 0% to about 50% of an immediate release particle containing a core comprising a therapeutically effective amount of at least one water-soluble or water-insoluble drug, about 15% to about 40% by weight inert spherical substrate particles, and about 0.5% to about 4% by weight binder, coated with about 4% to about 20% by weight talc and having a particle size of −10+60 mesh size, U.S. Standard sieve size, and b) up to 100% of an extended release particle comprising about 65% to about 95% by weight of the immediate release particle of a) additionally coated with about 5.0% to about 35% by weight of a dissolution modifying system comprising a film forming agent and plasticizer, wherein the extended release particle has a particle size of −10+60 mesh size, U.S. Standard sieve mesh size, and wherein all percentages are based on the total weight of the pharmaceutical formulation.

2. The extended release pharmaceutical formulation of claim 1, wherein the drug is selected from the group consisting of analgesics, anti-inflammatories, antihistamines, antitussives, expectorants, decongestants, narcotics, antibiotics, bronchodilators, cardiovasculars, central nervous system drugs, and mixtures thereof.

3. The extended release pharmaceutical formulation of claim 1, wherein the inert spherical substrate particles are selected from the group consisting of sugar spheres and non- toxic plastic resin beads.

4. The extended release pharmaceutical formulation of claim 1, which additionally contains preblended with the drug a non-toxic carrier selected from the group consisting of sugar, lactose, gelatin, starch, silicon dioxide and mixtures thereof.

5. The extended release pharmaceutical formulation of claim 1 wherein the binder is soluble in a solvent selected from water and an organic solvent.

6. The formulation of claim 5, wherein the binder is selected from the group consisting of povidone, pharmaceutical glaze, sugar, hydroxypropylmethylcellulose, hydroxypropylcellulose, ethylcellulose, acrylic and methacrylic acid co-polymers and mixtures thereof.

7. The extended release pharmaceutical formulation of claim 1 wherein the plasticizers which are used to form the extended release particle are selected from the group consisting of diethyl phthalate, diethyl sebacate, triethyl citrate, crotonic acid, propylene glycol, castor oil, citric acid esters, dibutyl phthalate, dibutyl sebacate and mixtures thereof.

8. The extended release pharmaceutical formulation of claim 1 wherein the film forming agent is selected from the group consisting of ethylcellulose, methylcellulose, hydroxypropylcellulose, cellulose acetate, hydroxypropylmethylcellulose, hydroxyethylcellulose and mixtures thereof.

9. The extended release pharmaceutical formulation of claim 1 wherein the immediate release particle contains a core comprising about 15 to about 40% inert spherical substrate particles, about 0.5 to about 4% binder and about 4 to about 85% drug, all percents herein are by weight of the final product.

10. The extended release pharmaceutical formulation of claim 2 wherein the expectorant is guaifenesin.

11. The extended release pharmaceutical formulation for oral administration, which comprises: a pharmaceutical formulation which is adapted to release a drug over a 12 to at least a 24 hour period, which formulation is comprised of a mixture of a) about 0% to about 50% of an immediate release particle containing a core comprising a therapeutically effective amount of at least one water-soluble or water-insoluble drug, about 15% to about 40% by weight inert spherical substrate particles, and about 0.5% to about 5% by weight binder, coated with about 4% to about 20% by weight talc and having a particle size of −10+60 mesh size, U.S. Standard sieve size, and b) up to 100% of an extended release particle comprising about 65% to about 95% by weight of the immediate release particle of a) additionally coated with about 5.0% to about 35% by weight of a dissolution modifying system comprising a film forming agent and plasticizer, wherein the extended release particle has a particle size of −10+60 mesh size, U.S. Standard sieve mesh size, and wherein all percentages are based on the total weight of the pharmaceutical formulation.

12. The formulation of claim 1, wherein the coating over the immediate release particle contains about 0.5 to about 25% film forming agent by weight, about 0.01 to about 5% plasticizer by weight, and up to 25% of porosity modifying agents.

13. The formulation of claim 1, wherein the dissolution modifying system of the immediate release particles contains additional amounts of drugs.

14. The extended release pharmaceutical formulation of claim 1, wherein the formulation is administered in the form of a tablet, capsule or particle form.

15. The extended release pharmaceutical formulation of claim 2, wherein the analgesics are selected from the group consisting of acetaminophen, ibuprofen, flurbiprofen, ketoprofen, phenacetin, voltaren and salicylamide.

16. The extended release pharmaceutical formulation of claim 2, wherein the anti-inflammatory drugs are selected from the group consisting of naproxen and indomethacin.

17. The extended release pharmaceutical formulation of claim 2, wherein the antihistamines are selected from the group consisting of chlorpheniramine maleate, phenindamine tartrate, pyrilamine maleate, doxylamine succinate, phenyltoloxamine citrate, diphenhydramine hydrochloride, promethazine, brompheniramine maleate, dexbrompheniramine maleate, clemastine fumerate, and triprolidine.

18. The extended release pharmaceutical formulation of claim 2, wherein the antitussives are selected from the group consisting of dextromethorphan hydrobromide and guaifenesin.

19. The extended release pharmaceutical formulation of claim 2, wherein the decongestants are selected from the group consisting of phenylephrine hydrochloride, phenypropanolamine hydrochloride, pseudoephedrine hydrochloride and ephedrine.

20. The extended release pharmaceutical formulation of claim 1, wherein the drug is phenylpropanolamine hydrochloride and chlorpheniramine maleate.

21. An extended release pharmaceutical formation for oral administration which comprises: a pharmaceutical formulation which is adapted to approach zero order release of drug over a 12 to at least 24 hour period, which formulation is comprised of a mixture of:
  a) 0 to about 50% of an immediate release particle containing about 15 to about 40% by weight inert spherical substrate particle about 0.5 to about 4% binder and about 4 to about 85% of at least one drug and a coating comprising about 4 to about 20% talc; and
  b) up to 100% of an extended release particle comprising an immediate release particle of a) coated with a dissolution modifying system comprising about 0.5 to about 25% film forming agent, about 0.01 to about 5% plasticizer and up to 25% modifying agent, all percents herein are by weight of the final product.

22. The extended release pharmaceutical formulation of claim 2, wherein the narcotics are selected from the group consisting of morphine, codeine and derivatives thereof.

23. The extended release pharmaceutical formulation of claim 2, wherein the antibiotics are selected from the group consisting of erythromycin, penicillins, cephalosporins and their derivatives.

24. The extended release pharmaceutical formulation of claim 2, wherein the bronchodilators are selected from the group consisting of theophylline, albuterol and terbutaline.

25. The extended release pharmaceutical formulation of claim 2, wherein the cardiovasculars are selected from the group consisting of diltiazem, propranolol, nifedepine and clonidine.

26. The extended release pharmaceutical formulation of claim 2, wherein the central nervous system drugs are selected from the group consisting of meclizine, ergoloid mesylates, thioridazine, diazepam, chlorpromazine, hydroxyzine, carbidopa and levodopa.

27. The extended release pharmaceutical formulation of claim 1, wherein the drug is pseudoephedrine hydrochloride and triprolidine.

28. The extended release pharmaceutical formulation of claim 1, wherein the drug is pseudoephedrine hydrochloride.

29. The extended release pharmaceutical formulation of claim 1, wherein the drug is pseudoephedrine hydrochloride and chlorpheniramine maleate.

* * * * *

UNITED STATES PATENT AND TRADEMARK OFFICE
CERTIFICATE OF CORRECTION

PATENT NO. : 5,133,974

DATED : JULY 28, 1992

INVENTOR(S) : George PARADISSIS et al.

It is certified that error appears in the above-identified patent and that said Letters Patent is hereby corrected as shown below:

Column 15, line 33, i.e., claim 6, line 3, change "hydroxpropylmethylcellulose" to --hydroxypropylmethylcellulose--.

Column 15, line 34, i.e., claim 6, line 4, change "hydroxpropylcellulose" to --hydroxypropylcellulose--.

Column 15, line 57, i.e., claim 11, line 1, change "The" to --An--.

Column 15, line 66, i.e., claim 11, line 10, change "5%" to --4%--.

Column 16, line 21, i.e., claim 14, line 3, change "particle" to --particulate--.

Column 16, line 46, i.e., claim 19, line 4, change "phenypropanolamine" to --phenylpropanolamine--.

UNITED STATES PATENT AND TRADEMARK OFFICE
CERTIFICATE OF CORRECTION

PATENT NO. : 5,133,974

DATED : JULY 28, 1992

INVENTOR(S) : George PARADISSIS et al.

It is certified that error appears in the above-identified patent and that said Letters Patent is hereby corrected as shown below:

Column 16, line 58, i.e., claim 21, line 8, after "particle" insert --,--.

Signed and Sealed this

Seventh Day of September, 1993

Attest:

BRUCE LEHMAN

Attesting Officer

Commissioner of Patents and Trademarks